United States Patent
Cruz et al.

(10) Patent No.: US 8,226,979 B2
(45) Date of Patent: Jul. 24, 2012

(54) DRUG COATING PROVIDING HIGH DRUG LOADING AND METHODS FOR PROVIDING THE SAME

(75) Inventors: Evangeline Cruz, Hayward, CA (US); Gregory Ruhlmann, Cupertino, CA (US); Brenda Pollock, Cupertino, CA (US); Sherry Li, Cupertino, CA (US); Carmelita Garcia, Newark, CA (US); Alfredo M. Wong, Sunnyvale, CA (US); Ryan Bronz, Cupertino, CA (US); Tracy Fink, Campbell, CA (US); David Edgren, Los Altos, CA (US)

(73) Assignee: Alza Corporation, Vacaville, CA (US)

( * ) Notice: Subject to any disclaimer, the term of this patent is extended or adjusted under 35 U.S.C. 154(b) by 0 days.

(21) Appl. No.: 13/084,462

(22) Filed: Apr. 11, 2011

(65) Prior Publication Data

US 2011/0318392 A1 Dec. 29, 2011

Related U.S. Application Data

(63) Continuation of application No. 10/950,003, filed on Sep. 23, 2004.

(60) Provisional application No. 60/506,195, filed on Sep. 26, 2003.

(51) Int. Cl.
  *A61K 9/24* (2006.01)
  *A61K 9/22* (2006.01)
  *A61K 9/54* (2006.01)

(52) U.S. Cl. ......... 424/464; 424/458; 424/468; 424/472

(58) Field of Classification Search ........................ None
See application file for complete search history.

(56) References Cited

U.S. PATENT DOCUMENTS

| | | |
|---|---|---|
| 2,799,241 A | 7/1957 | Wurster et al. |
| 3,133,132 A | 5/1964 | Loeb et al. |
| 3,173,876 A | 3/1965 | Zobrist et al. |
| 3,173,877 A | 3/1965 | Jackson et al. |
| 3,276,586 A | 10/1966 | Rosaen et al. |
| 3,480,616 A | 11/1969 | Osipow et al. |
| 3,541,005 A | 11/1970 | Strathmann et al. |
| 3,541,006 A | 11/1970 | Bixler et al. |
| 3,546,142 A | 12/1970 | Michaels et al. |
| 3,845,770 A | 11/1974 | Theeuwes et al. |
| 3,865,108 A | 2/1975 | Hartop et al. |
| 3,916,899 A | 11/1975 | Theeuwes et al. |
| 3,995,631 A | 12/1976 | Higuchi et al. |
| 4,002,173 A | 1/1977 | Manning et al. |
| 4,008,719 A | 2/1977 | Theeuwes et al. |
| 4,034,756 A | 7/1977 | Higuchi et al. |
| 4,063,064 A | 12/1977 | Saunders et al. |
| 4,077,407 A | 3/1978 | Theeuwes et al. |
| 4,088,864 A | 5/1978 | Theeuwes et al. |
| 4,111,201 A | 9/1978 | Theeuwes et al. |
| 4,111,202 A | 9/1978 | Theeuwes et al. |
| 4,160,020 A | 7/1979 | Ayer et al. |
| 4,200,098 A | 4/1980 | Ayer et al. |
| 4,207,893 A | 6/1980 | Michaels et al. |
| 4,235,236 A | 11/1980 | Theeuwes et al. |
| 4,278,087 A | 7/1981 | Theewes |
| 4,285,987 A | 8/1981 | Ayer et al. |
| 4,320,759 A | 3/1982 | Theeuwes et al. |
| 4,327,725 A | 5/1982 | Cortese et al. |
| 4,449,983 A | 5/1984 | Cortese et al. |
| 4,464,378 A | 8/1984 | Hussain |
| 4,519,801 A | 5/1985 | Edgren et al. |
| 4,576,604 A | 3/1986 | Guittard et al. |
| 4,578,075 A | 3/1986 | Urquhart et al. |
| 4,612,008 A | 9/1986 | Wong et al. |
| 4,663,149 A | 5/1987 | Eckenhoff et al. |
| 4,681,583 A | 7/1987 | Urquhart et al. |
| 4,717,569 A | 1/1988 | Harrison et al. |
| 4,763,405 A | 8/1988 | Morita et al. |
| 4,765,989 A | 8/1988 | Wong et al. |
| 4,777,049 A | 10/1988 | Magruder et al. |
| 4,783,337 A | 11/1988 | Wong et al. |
| 4,786,503 A | 11/1988 | Edgren et al. |
| 4,801,461 A | 1/1989 | Hamel et al. |
| 4,806,359 A | 2/1989 | Radebaugh et al. |
| 4,816,470 A | 3/1989 | Dowle et al. |
| 4,820,522 A | 4/1989 | Radebaugh et al. |
| 4,844,907 A | 7/1989 | Elger et al. |

(Continued)

FOREIGN PATENT DOCUMENTS

AU    2003 301121 A1    7/2004

(Continued)

OTHER PUBLICATIONS

U.S. Appl. No. 60/570,981, filed May 14, 2004, Cruz et al.

(Continued)

*Primary Examiner* — Robert A Wax
*Assistant Examiner* — Jeffrey T Palenik
(74) *Attorney, Agent, or Firm* — Samuel M. Kais

(57) ABSTRACT

The present invention is directed to aqueous drug coatings that include at least one insoluble drug, wherein the drug accounts for about 85 wt % to about 97 wt % of the drug coatings. A drug coating according to the present invention may include only one insoluble drug, two or more insoluble drugs, or one or more insoluble drugs in combination with one or more soluble drugs. The present invention also includes drug coating formulations suitable for providing drug coatings according to the present invention and dosage forms that include a drug coating according to the present invention.

4 Claims, 3 Drawing Sheets

U.S. PATENT DOCUMENTS

| | | |
|---|---|---|
| 4,847,077 A | 7/1989 | Raghunathan |
| 4,854,470 A | 8/1989 | Ireland et al. |
| 4,892,778 A | 1/1990 | Theeuwes et al. |
| 4,915,949 A | 4/1990 | Wong et al. |
| 4,915,954 A | 4/1990 | Ayer et al. |
| 4,931,285 A | 6/1990 | Edgren et al. |
| 4,940,465 A | 7/1990 | Theeuwes et al. |
| 4,946,675 A | 8/1990 | Baldwin et al. |
| 4,946,685 A | 8/1990 | Edgren et al. |
| 4,961,932 A | 10/1990 | Theeuwes |
| 4,968,509 A | 11/1990 | Radebaugh et al. |
| 5,004,613 A | 4/1991 | Radebaugh et al. |
| 5,006,346 A | 4/1991 | Edgren et al. |
| 5,019,397 A | 5/1991 | Wong et al. |
| 5,021,053 A | 6/1991 | Barclay et al. |
| 5,023,088 A | 6/1991 | Wong et al. |
| 5,024,842 A | 6/1991 | Edgren et al. |
| 5,030,456 A | 7/1991 | Ayer et al. |
| 5,126,142 A | 6/1992 | Ayer et al. |
| 5,156,850 A | 10/1992 | Wong et al. |
| 5,160,743 A | 11/1992 | Edgren et al. |
| 5,166,145 A | 11/1992 | Jao et al. |
| 5,190,765 A | 3/1993 | Jao et al. |
| 5,200,193 A | 4/1993 | Radebaugh et al. |
| 5,221,536 A | 6/1993 | Edgren et al. |
| 5,252,338 A | 10/1993 | Jao et al. |
| 5,273,760 A | 12/1993 | Oshlack et al. |
| 5,286,493 A | 2/1994 | Oshlack et al. |
| 5,340,590 A | 8/1994 | Wong et al. |
| 5,407,686 A | 4/1995 | Patel et al. |
| 5,417,682 A | 5/1995 | Wong et al. |
| 5,460,826 A | 10/1995 | Merrill et al. |
| 5,512,299 A | 4/1996 | Place et al. |
| 5,529,787 A | 6/1996 | Merrill et al. |
| 5,534,263 A | 7/1996 | Wong et al. |
| 5,593,695 A | 1/1997 | Merrill et al. |
| 5,614,578 A | 3/1997 | Dong et al. |
| 5,620,705 A | 4/1997 | Dong et al. |
| 5,633,011 A | 5/1997 | Dong et al. |
| 5,660,861 A | 8/1997 | Jao et al. |
| 5,667,804 A | 9/1997 | Wong et al. |
| 5,702,725 A | 12/1997 | Merrill et al. |
| 5,830,502 A | 11/1998 | Dong et al. |
| 5,858,407 A | 1/1999 | Ayer et al. |
| 5,866,161 A | 2/1999 | Childers et al. |
| 5,866,164 A | 2/1999 | Kuczynski et al. |
| 5,906,832 A | 5/1999 | Jao et al. |
| 5,912,268 A | 6/1999 | Guittard et al. |
| 5,914,131 A | 6/1999 | Merrill et al. |
| 5,948,747 A | 9/1999 | Schambil |
| 5,948,787 A | 9/1999 | Merrill et al. |
| 5,993,858 A | 11/1999 | Crison et al. |
| 5,998,478 A | 12/1999 | Platt et al. |
| 6,004,582 A | 12/1999 | Faour et al. |
| 6,020,000 A | 2/2000 | Wong et al. |
| 6,132,420 A | 10/2000 | Dionne et al. |
| 6,136,345 A | 10/2000 | Grimmett et al. |
| 6,153,678 A | 11/2000 | Dong et al. |
| 6,174,547 B1 | 1/2001 | Dong et al. |
| 6,183,466 B1 | 2/2001 | Wong et al. |
| 6,210,714 B1 | 4/2001 | Oshlack et al. |
| 6,228,863 B1 | 5/2001 | Palermo et al. |
| 6,245,357 B1 | 6/2001 | Edgren et al. |
| 6,245,657 B1 | 6/2001 | Chu et al. |
| 6,254,891 B1 | 7/2001 | Anaebonam et al. |
| 6,270,787 B1 | 8/2001 | Ayer et al. |
| 6,283,953 B1 | 9/2001 | Ayer et al. |
| 6,284,274 B1 | 9/2001 | Merrill et al. |
| 6,287,295 B1 | 9/2001 | Chen et al. |
| 6,316,028 B1 | 11/2001 | Wong et al. |
| 6,333,050 B2 | 12/2001 | Wong et al. |
| 6,342,245 B1 | 1/2002 | Baert et al. |
| 6,342,249 B1 | 1/2002 | Wong et al. |
| 6,365,183 B1 | 4/2002 | Edgren et al. |
| 6,368,626 B1 | 4/2002 | Bhatt et al. |
| 6,375,978 B1 | 4/2002 | Kleiner et al. |
| 6,387,404 B2 | 5/2002 | Oshlack et al. |
| 6,491,683 B1 | 12/2002 | Dong et al. |
| 6,491,945 B1 | 12/2002 | Childers et al. |
| 6,491,949 B2 | 12/2002 | Faour et al. |
| 6,586,458 B1 | 7/2003 | Plachetka et al. |
| 6,592,900 B1 | 7/2003 | Buhler et al. |
| 6,610,323 B1 | 8/2003 | Lundberg et al. |
| 6,669,955 B2 | 12/2003 | Chungi et al. |
| 6,893,660 B2 | 5/2005 | Li et al. |
| 7,195,778 B2 | 3/2007 | Fleshner-Barak et al. |
| 7,457,343 B2 | 11/2008 | Vancoille |
| 2001/0012847 A1 | 8/2001 | Lam et al. |
| 2001/0024658 A1 | 9/2001 | Chen et al. |
| 2001/0026809 A1 | 10/2001 | Chasin et al. |
| 2001/0031279 A1 | 10/2001 | Cruz et al. |
| 2002/0058050 A1 | 5/2002 | Sackler et al. |
| 2002/0071863 A1 | 6/2002 | Dong et al. |
| 2003/0044457 A1* | 3/2003 | Faour et al. .................. 424/458 |
| 2003/0077320 A1 | 4/2003 | Childers et al. |
| 2003/0092724 A1 | 5/2003 | Kao et al. |
| 2003/0190358 A1 | 10/2003 | Oshlack et al. |
| 2003/0198619 A1 | 10/2003 | Dong et al. |
| 2003/0224051 A1 | 12/2003 | Fink et al. |
| 2003/0232078 A1 | 12/2003 | Dong et al. |
| 2004/0056337 A1 | 3/2004 | Hasebe et al. |
| 2004/0247677 A1 | 12/2004 | Oury et al. |
| 2005/0089750 A1 | 4/2005 | Ng et al. |
| 2005/0112195 A1 | 5/2005 | Cruz et al. |
| 2005/0158382 A1 | 7/2005 | Cruz et al. |
| 2006/0099257 A1 | 5/2006 | Langridge et al. |
| 2006/0251721 A1 | 11/2006 | Cruz et al. |
| 2007/0259033 A1 | 11/2007 | Cruz et al. |
| 2007/0281018 A1 | 12/2007 | Qiu et al. |
| 2008/0031901 A1 | 2/2008 | Qiu et al. |

FOREIGN PATENT DOCUMENTS

| | | |
|---|---|---|
| EP | 005 129 A1 | 4/1979 |
| EP | 005 129 B1 | 4/1979 |
| EP | 166 287 A1 | 6/1985 |
| EP | 166 287 B1 | 6/1985 |
| EP | 174 726 A1 | 7/1985 |
| EP | 174 726 B1 | 7/1985 |
| EP | 0 220 805 B1 | 5/1987 |
| EP | 0 293 066 B1 | 2/1988 |
| EP | 379314 A1 | 1/1990 |
| EP | 379314 B1 | 1/1990 |
| EP | 0 367 746 B1 | 5/1990 |
| EP | 0 377 518 | 7/1990 |
| EP | 0 475 536 B1 | 3/1992 |
| EP | 0 631 781 A1 | 1/1995 |
| EP | 0 958 812 A1 | 11/1999 |
| EP | 1 027 888 A2 | 1/2000 |
| GB | 2 163 747 A | 8/1985 |
| JP | 4 501425 T | 5/1990 |
| JP | 5194227 A | 9/1992 |
| JP | 8 502516 T | 10/1993 |
| JP | 7 112932 A | 8/1994 |
| JP | 8 509480 T | 11/1994 |
| JP | 2000 516610 T | 2/1998 |
| JP | 2002 513392 T | 6/1998 |
| JP | 2000 516637 T | 12/1998 |
| JP | 2002 505274 | 9/1999 |
| JP | 2002-528486 T | 11/1999 |
| JP | 2002 523358 T | 3/2000 |
| JP | 2002 528505 T | 5/2000 |
| JP | 2002 531499 T | 6/2000 |
| JP | 2003 509354 T | 3/2001 |
| JP | 2001 527034 T | 12/2001 |
| NZ | 546182 | 4/2005 |
| NZ | 568198 | 4/2005 |
| WO | WO 90 04965 | 5/1990 |
| WO | WO 90/06925 A1 | 6/1990 |
| WO | WO 91 19711 A1 | 12/1991 |
| WO | WO 91 19712 A2 | 12/1991 |
| WO | WO 92 04012 A1 | 3/1992 |
| WO | WO 93 24154 | 12/1993 |
| WO | WO 94 27988 A1 | 12/1994 |
| WO | WO 95 14460 A1 | 6/1995 |
| WO | WO 95 34285 A1 | 12/1995 |
| WO | WO 96 01629 | 1/1996 |
| WO | WO 96 10996 | 4/1996 |

| | | |
|---|---|---|
| WO | WO 96 35414 A1 | 11/1996 |
| WO | WO 98 06380 A2 | 2/1998 |
| WO | WO 98 14168 | 4/1998 |
| WO | WO 98 23263 | 6/1998 |
| WO | WO 99 44591 | 9/1999 |
| WO | WO 99 55313 A1 | 11/1999 |
| WO | WO 99 62496 A1 | 12/1999 |
| WO | WO 00 35426 A2 | 6/2000 |
| WO | WO 01 32148 | 5/2001 |
| WO | WO 01 51038 A1 | 7/2001 |
| WO | WO 02 05647 A1 | 1/2002 |
| WO | WO 02 34240 A2 | 5/2002 |
| WO | WO 02 087512 A2 | 11/2002 |
| WO | WO 03 092648 | 1/2003 |
| WO | WO 03 101384 | 12/2003 |
| WO | WO 2004 002448 A1 | 1/2004 |
| WO | WO 2004 010970 A1 | 2/2004 |
| WO | WO 2004 024921 A1 | 3/2004 |
| WO | WO 2004 056337 A1 | 7/2004 |
| WO | WO 95 01977 A1 | 1/2005 |
| WO | WO 2005 011630 A2 | 2/2005 |
| WO | WO 2005 030166 A1 | 4/2005 |
| WO | WO 2005 030181 A1 | 4/2005 |
| WO | WO 2005 030182 A1 | 4/2005 |
| WO | WO 2005 072079 A3 | 8/2005 |
| WO | WO 2007 085024 A2 | 7/2007 |
| WO | WO 2008 011169 A2 | 1/2008 |

OTHER PUBLICATIONS

U.S. Appl. No. 60/506,195, filed Sep. 26, 2003, Cruz et al.
U.S. Appl. No. 60/497,162, filed Aug. 22, 2003, Yam et al.
U.S. Appl. No. 60/571,045, filed May 14, 2004, Cruz et al.
U.S. Appl. No. 60/571,238, filed May 14, 2004, Cruz et al.
U.S. Appl. No. 10/949,141, filed Sep. 14, 2004, Cruz et al.
U.S. Appl. No. 10/949,687, filed Sep. 24, 2004, Cruz et al.
U.S. Appl. No. 10/949,180, filed Sep. 24, 2004, Cruz et al.
Hixon "Sizing Chemicals by Crushing and Grinding" Chemical Engineering 1990 pp. 94-103.
Jackson et al. "Drug-Excipient Interactions and Their Affect on Absorption", Pharm Sci. Technology Today 2000 vol. 3(10) pp. 336-345.
McCutcheon's Detergents and Emulsifiers International Ed 1979.
McCutcheon's Detergents and Emulsifiers North American Ed Ed 1979.
Nandi et al. "Synergistic Effect of PEG-400 and Cyclodextrin to Enhance Solubility of Progesterone", AAPS Pharm Sci Tech 2003 vol. 4(1):pp. E1.
Ripple et al "Powders" Pharmaceutical Sciences Remington 17 Ed 1985 Chapter 89 pp. 1585-1594.
Rouse et al "Cellulose Esters Organic" Encyclopedia of Polymer Science and Technology 1964 vol. 3 pp. 325-354.
Santus and Baker "Osmotic Drug Delivery: A Review of the Patent Literature" Journal of Controlled Release 1995 vol. 35 pp. 1-21.
Scott and Roff Handbook of Common Polymers 1971 Chemical Rubber Co Cleveland OH.
Wurster Dale Air Suspension Technique of Coating Drug Particles: Journal of American Pharmaceutical Association 1959 vol. 48 pp. 451-459.
Wurtster Dale "Preparation of Compressed Tablet Granulations by the Air Suspension Technique LL" J Am Pharm Assoc 1960 vol. 49(2) pp. 82-84.
Marcel Dekker Inc "Treatise on Controlled Drug Delivery Fundamentals Optimization Application" 1992 Agis Kydonieus Ed New York NY.
Marcel Dekker Inc "Handbook of Pharmaceutical Controlled Release Technology" 2000 Donald L. Wise Ed. New York NY.
Remington's Pharmaceutical Sciences 18$^{th}$ Ed 1990 PS 1635-1637.
McNeil Background Package on Acetaminophen for the Sep. 19, 2002 Nonprescription Drug Advisory Committee Meeting That Was Annoucned in the Federal Register of August 20, 2002. Available at http://www.fda.gov/ohrms/docket/ac/02/briefing/3882BI_13_ Mcneil_Acetaminophen.pdf and accessed Mar. 14, 2006.
Barkin "Acetaminophen, Aspirin, or Ibuprofen in Combination Analgesic Products", American Journa of Therapeutics 2001 vol. 8 pp. 433-442.
Cao, Quing-Ri "Formulation, Release Characteristics and Bioavailability of Novel Monolithic Hydroxypropylmethylcellulose Matrix Tablets Coating Acetaminophen", Journal of Controlled Release 2005 vol. 108(2-3) pp. 351-361.
Dalton J. T. et al "Predictivie Ability of Level A In Vitro-In-Vivo Correlation for Ringcap Controlled-Release Acetaminophen Tablets", Pharmaceutical Research 2001 vol. 18(12) pp. 1729-1734.
Donbrow and Friedman "Enhancement of Permeability of Ethyl Cellulose Films for Drug Penetration" J Pharm Pharmacol 1975 vol. 27 pp. 633-646.
Donbrow and Samuelov "Zero Order Drug Delivery From Double-Layered Porous Films: Release Rate Profiles for Ethyl Cellulose Hydroxypropyl Cellulose and Polyethylene Glycol Mixtures" J Pharm Pharmacol, 1989 vol. 32 pp. 463-470.
Fried R.F. In Polymer Science and Technology (Englewood Cliffs NJ 07632, Prentice Hall PTR 1995 pp. 16-18.
Gimbel "Efficacy and Tolerability of Celecoxib Versus Hydrocodone/Acetaminophen in the Treatment of Pain After Ambulatory Orthopedic Surgery in Adults" Clinical Therapeutics 2001 vol. 23(2) pp. 228-241.
Glaxosmithkline Submission to the Medicines Classification Committee for Reclassification of a Medicine, Classification of Paracetamol in Modified Release Tablets Containing 665 MG or Less as a Pharmacy Only Medicines 2001 pp. 1-21.
Heading et al "The Dependence of Paracetamol Absorption on the Rate of Gastric Emptying" British Journal of Pharmacology 1973 vol. 47 pp. 415-421.
Hiemenz et al "The Chains and Averages of Polymers" in Polymer Chemistry the Basic Concepts NY Marcell Dekker Inc 1984 pp. 34-43.
Higuchi et al "Rate of Release of Medicaments From Ointment Bases Containing Drug in Suspension" Journal of Pharmaceutical Sciences 1961 vol. 50 pp. 874-875.
Kimura et al "Drug Absorption From Large Intestines: Physicochemical Factors Governing Drug Absorption" Biol Pharm Bull 1994 vol. 17(2) pp. 327-333.
Krishnaiah et al "A Three Layer Guar Gum Matrix Tablet for Oral Controlled Delivery of Highly Soluble Metoprolol Tartrate" International Journal of Pharmaceutics 2002 vol. 241 pp. 353-366.
Mandelkern et al "Structural Features and Preparation" in an Introduction to Macromolecules 2$^{nd}$ Ed. Springer-Verlag, New York Inc. 1983 pp. 19-27.
McGraw-Hill "Introduction OT Screening and Wet Classification" Perry's Chemical Engineers Handbook 6$^{th}$ Ed. 1984 pp. 21-13 to 21-19.
Nikitin et al "A General Survey of Physiochemical Properties of Cellulose" in the Chemistry of Cellulose and Wood (Jerusalem 1966) pp. 62-71.
O'Connor et al "Powders" Remington'S Pharmaceutical Sciences 18$^{th}$ Ed. 1990 Chapter 88 pp. 1615-1632.
Ofori-Kwayke et al "Gamma Scintigraphic Evaluation of Film-Coated Tablets Intended for Colonic or Biphasic Release" International Journal of Pharmaceutics 2004 vol. 270 pp. 307-313.
Parrott et al "Milling of Pharmaceutical Solids" Journal of Pharmaceutical Sciences 1974 vol. 63 pp. 813-829.
Qiu et al "Design and Evaluation of Layered Diffusional Matrices for Zero-Order Sustained-Release" Journal of Controlled Release 1998 vol. 51 pp. 123-130.
Rowe et al The Effect of the Molecular Weight of Ethyl Cellulose and Hydroxypropyl Methylcellulose International Journal of Pharmaceutics 1986 vol. 29 pp. 37-41.
Sako et al "Influence of Water Soluble Fillers in Hydroxypropylmethylcellulose Matrices on In Vitro and In Vivo Drug Release" Journal of Controlled Release 2002 vol. 81 pp. 165-172.
Sawada et al "A New Index, The Core Erosion Ratio of Compression-Coated Timed-Release Tablets Predics the Bioavailability of Acetaminophen" International Journal of Pharmaceutics 2003 vol. 265 pp. 55-63.
Shimono et al "Chitosam Dispersed System for Colon-Specific Drug Delivery" International Journal of Pharmaceutics 2002 vol. 245 pp. 45-54.

The Handbook of Pharmaceutical Excipients "Microcrystalline Cellulose" 1986 1st Ed. pp. 53-55.

The Handbook of Pharmaceutical Excipients "Hydroxypropyl Methylcellulose" 1986 1st Ed. pp. 138-140.

The Handbook of Pharmaceutical Excipients "Copovidone" 2006 5th Ed. pp. 201.

Torrado et al "Correlation of In Vitro and In Vivo Acetaminophen Availability From Albumin Microaggregates Oral Modified Release Formulations" International Journal of Pharmaceutics 2001 vol. 217 pp. 193-199.

Watson Pharma NORCO® (Hydrocodone Bitartrate and Acetaminophen Tablets USP) Apr. 2002.

Yamada et al "Evaluation of Gastrointestinal Transit Controlled Beagle Dog as Asuitable Animal Model for Bioavailability Testing of Sustained Release Acetaminophen Dosage Form" International Journal of Pharmaceutics 1995 vol. 119 pp. 1-10.

Vicodin Hydrocodone Bitartrate and Acetaminophen Drug Information User Review Last Review Jan. 24, 2011 http://www.rxlist.com/vicodin-drug.htm accessed Jun. 28, 2011.

* cited by examiner

DRUG COATING PROVIDING HIGH DRUG LOADING AND METHODS FOR PROVIDING THE SAME

CROSS-REFERENCE TO RELATED APPLICATIONS

This application is continuation of U.S. Ser. No. 10/950,003 filed Sep. 23, 2004, which claims the benefit under 35 USC §119(e) of the following provisional application: U.S. Ser. No. 60/506,195, filed Sep. 26, 2003. The complete disclosures of the aforementioned related U.S. patent applications are hereby incorporated herein by reference for all purposes.

BACKGROUND

1. Field of the Invention

The present invention relates to drug coatings that can be formed within or over dosage forms to deliver one or more insoluble or soluble drugs. In particular, the present invention provides drug coatings, coating formulations and methods that provide aqueous-based drug coatings that exhibit high loading of at least one insoluble drug, can be loaded with one or more insoluble drugs in combination with one or more insoluble drugs, and may be applied to a variety of different dosage forms.

2. State of the Art

Drug coatings are known in the art. For example, U.S. Pat. Nos. 4,576,604, 4,717,569, 4,763,405, 5,273,760, 5,286,493, 5,407,686, 5,998,478, 6,004,582 and 6,136,345, the contents of each of which are incorporated herein in their entirety by reference, teach various different drug coating formulations designed to provide the immediate release of one or more drugs of interest. In addition, International Applications numbered WO 96/10996, WO 99/55313, WO 00/35426 and WO 01/51038, the contents of which are incorporated herein in their entirety by reference, also teach various different drug coating formulations that may be provided over various different dosage forms. Drug coatings that can be coated over dosage forms are useful for a variety of reasons. In particular, the use of a drug-containing overcoat can impart multiple performance characteristics to a single dosage form. For example, a dosage form providing the controlled release of one or more drugs can be coated with an immediate release drug overcoat to provide a dosage form that combines the benefits of an immediate release dosage form with the benefits of a controlled release dosage form.

Where a coating formulation is to be used to provide a drug coating over or within a dosage form, the coating formulation should provide drug loading characteristics that permit therapeutic dosing of the drug incorporated in the coating, while maintaining desirable coating characteristics. The loading characteristics of a drug coating become especially important as the desired dose of drug to be delivered from the drug coating increases. As the required dose increases, the drug loading performance of the drug coating formulation must also increase. If the drug coating formulation does not exhibit sufficient drug loading, the thickness of a coating required to deliver a desired dose of drug may increase to such an extent that manufacturing, cosmetic, and patient compliance issues may be encountered.

Moreover, although, drug coatings can be prepared from organic solvents or solvent systems containing one or more organic solvents, the use of organic solvents presents several potential disadvantages. Organic solvents are relatively costly, often volatile, are potentially harmful to the environment, and create potential health hazards for workers. Because of the potential harm organic solvents present to workers and the environment, the use of organic solvents in a manufacturing process typically creates various regulatory hurdles that must be overcome. Moreover, where organic solvents are used to produce drug coatings, some residual amount of solvent may remain in the finished coating, which, depending on the amount and the solvent used, may be harmful to an intended subject. In light of the potential disadvantages presented by organic solvents, it is generally preferred to formulate drug coatings and coating compositions using solvents or solvent systems that do not include organic solvents In particular, where possible, it is typically preferable to formulate drug coatings using an aqueous solvent, such as purified water. It would be desirable, therefore, to provide a drug coating that not only can be coated from an aqueous coating composition, but also exhibits drug loading capabilities that facilitate delivery of a wide range of drug doses from coatings having physical and aesthetic characteristics suitable for commercial production. Ideally, such a drug coatings could be formulated to include high concentrations of even water insoluble drugs, or combinations of one or more water insoluble drugs with one or more water soluble drugs.

SUMMARY OF THE INVENTION

In one aspect, the present invention is directed to an aqueous drug coating. As it is used herein, the term "aqueous drug coating" refers to a water soluble or water erodible coating formed from a coating formulation that is free from organic solvent. A drug coating according to the present invention can be created from an aqueous coating formulation and includes at least one insoluble drug and a film-forming agent. As they are used herein, the term "drug" includes medicines, active agents, therapeutic compounds, therapeutic proteins, therapeutic peptides, nutrients, vitamins, food supplements, and any other agents that are beneficial to an intended subject, the term "insoluble" indicates drugs having a solubility in water that is less than 50 mg/ml at 25° C., with drugs having a solubility in water of 8-10 mg/ml at 25° C. being preferred, and drugs having a solubility in water of less than 1 mg/ml at 25° C. being particularly preferred. The drug coating according to the present invention includes from about 85 wt % to about 97 wt % drug, with preferred embodiments providing a drug loading of about 90 wt % to about 93 wt %.

Though each embodiment of the drug coating of the present invention includes at least one insoluble drug, the drug coating of the present invention is also embodied by drug coatings that include two or more insoluble drugs or one or more insoluble drugs in combination with one or more soluble drugs. As it is used herein, the term "soluble" indicates drugs having a solubility in water that is 50 mg/ml or greater at 25° C. Where the drug coating of the present invention includes more than one drug, the different drugs may be included in the drug coating at a ratio that provides a desired therapeutic effect. Moreover, the formulation of a drug coating of the present invention not only allows the loading of two or more drugs have different solubilities, but following administration to an environment of operation, a drug coating of the present invention permits proportional delivery of the two or more drugs included therein.

In another embodiment, the drug coating according to the present invention includes a viscosity enhancer. As it is used herein, the term "viscosity enhancer" refers to a material that can be included in a composition for forming a drug coating of the present invention that is both water soluble and works to increase the viscosity of the coating composition. Depending on the relative amounts and nature of the film forming agent and the one or more drugs included in a drug coating of the present invention, incorporation of a viscosity enhancer in a drug coating according to the present invention may better facilitate production of a drug coating that exhibits substantially uniform distribution of drug.

In further embodiments embodiment, the drug coating of the present invention may also include a surfactant or a disintegrating agent. The term "surfactant" refers to material that is works to reduce the surface tension of aqueous liquids such that an aqueous liquid can more easily spread across and penetrate the materials forming a drug coating according to the present invention, and the term "disintegrating agent" refers to a water swellable material that works to structurally compromise a coating of the present invention as the disintegrating agent absorbs water and swells. In each embodiment, the drug coating according to the present invention provides relatively high drug loading, and in each embodiment, the drug coating according to the present invention includes at least one insoluble drug. Therefore, a surfactant or disintegrating agent may be included in a drug coating of the present invention to facilitate break down or dissolution of the drug coating after administration to an environment of operation and thereby increase the rate at which the drug included in the drug coating is released.

In another aspect the, the present invention is directed to a drug coating formulation. A coating formulation according to the present invention is an aqueous composition, preferably formed using purified water as the solvent. The coating composition of the present invention is formulated to allow coating of a drug coating according to the present invention, and in each embodiment, the coating formulation of the present invention includes at least one insoluble drug. As the coating formulation of the present invention is an aqueous formulation that includes at least one insoluble drug, the coating formulation of the present invention will typically be formed as a dispersion, with coating formulations exhibiting a substantially uniform dispersion of insoluble drug being preferred. The coating composition according to the present invention may be formulated to facilitate spray coating of a drug coating of the present invention, and typically includes a solids content ranging up to 30 wt %, with coating compositions having a solids content ranging from about 5 wt % to about 25 wt % being preferred, and coating compositions having a solids content ranging from about 10 wt % to about 20 wt % being particularly preferred.

In yet another aspect, the present invention is directed to a dosage form. A dosage form according to the present invention includes or is coated with a drug coating according to the present invention. In particular, a dosage form according to the present invention includes a core coated by a drug coating of the present invention. The core included in a dosage form according to the present invention can be formed using any material or device suitable for administration to an intended subject. For example, the core included in a dosage form of the present invention may includes a pill, a tablet or a capsule, and in preferred embodiments the pill, tablet or capsule included in the core is configured or formulated to provided controlled release of one or more drugs. Where the dosage form of the present invention includes a core the provides controlled release of one or more drugs, the dosage form according to the present invention can be configured and formulated to provide the combined benefits of an immediate release dosage form and a controlled release dosage form.

DETAILED DESCRIPTION OF THE INVENTION

Figure 1:
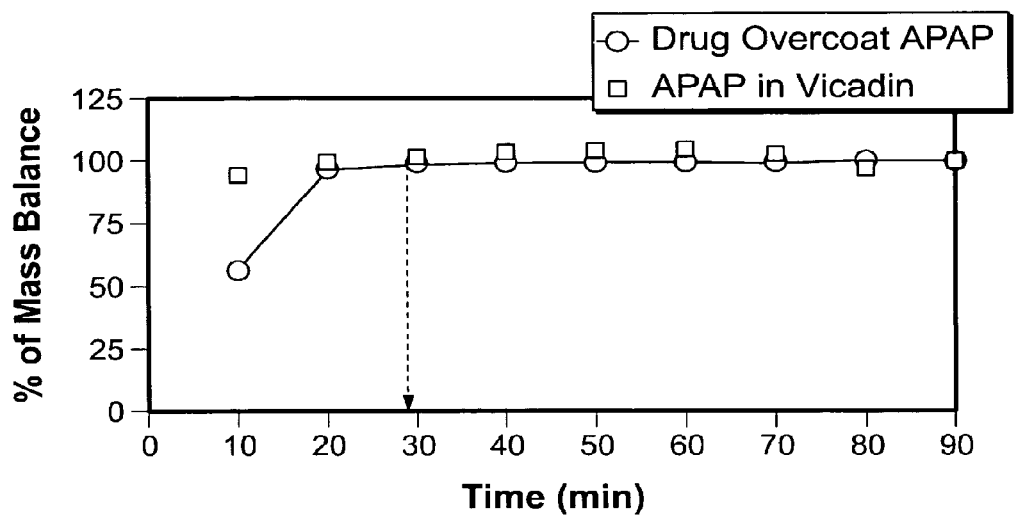
FIG. 1 provides a graph illustrating the dissolution rate of acetaminophen (APAP) from a drug coating according to the present invention compared to the dissolution rate of APAP from a commercially available Vicodin® tablet.

In one aspect, the present invention is directed to an aqueous drug coating. A drug coating according to the present invention can be formed from an aqueous coating formulation and includes an insoluble drug and a water soluble, film-forming agent. Though each embodiment of a drug coating according to the present invention includes an insoluble drug, a drug coating according to the present invention may also include an insoluble drug in combination with a soluble drug. Moreover, a drug coating according to the present invention may incorporate, for example, two or more insoluble drugs, an insoluble drug in combination with one or more soluble drugs, or two or more insoluble drugs in combination with one or more soluble drugs. The total amount of drug included in a drug coating according to the present invention ranges from about 85 wt % to about 97 wt %, and in preferred embodiments, the total amount of drug included in a drug coating of the present invention ranges from about 90 wt % to about 93 wt %.

Even where the drug coating of the present invention includes only insoluble drug material, the one or more insoluble drugs can account for up to about 97 wt % of the drug coating. In preferred embodiments, the drug coating of the present invention includes from about 85 wt % to about 97 wt % insoluble drug, with coatings exhibiting an insoluble drug loading of about 90 wt % to about 93 wt % being particularly preferred. If two or more insoluble drugs are included in a drug coating according to the present invention, the relative amounts of each insoluble drug can vary, depending on the nature of the insoluble drugs used. Moreover, the relative amounts of two or more insoluble drugs included in a drug coating according to the present invention can be adjusted, as necessary, to achieve a desired therapeutic effect.

Where a drug coating according to the present invention includes one or more insoluble drugs in combination with one or more soluble drugs, the relative amounts of the soluble and insoluble drugs included in the coating can vary, depending on the nature of the drug materials, and can be adjusted to achieve a desired therapeutic effect. The total amount of soluble drug included in a drug coating according to the present invention that incorporates both soluble and insoluble drugs preferably ranges from about 0.01 wt % to about 25 wt %, with drug coatings including about 0.5 wt % to about 15 wt % soluble drug being more preferred, and drug coatings including about 1 wt % to about 3 wt % soluble drug being most preferred. The total amount of insoluble drug included in a drug coating according to the present invention that incorporates both soluble and insoluble drugs preferably ranges from about 60 wt % to about 96.99 wt %, with drug coatings including about 75 wt % to about 89.5 wt % insoluble drug being more preferred, and drug coatings including about 89 wt % to about 90 wt % insoluble drug being most preferred.

A wide range of insoluble drugs may be incorporated into a drug coating according to the present invention. In one embodiment, the insoluble drug included in a drug coating according to the present invention may be a non-steroidal anti-inflammatory drug, with acetaminophen or ibuprofen being particularly preferred insoluble drugs. Preferably, the insoluble drug included in a drug coating of the present invention exhibits solubility characteristics similar those of acetaminophen at 25° C. or to those of ibuprofen at 25° C.

A variety of different soluble drugs can also be used to create a drug coating according to the present invention. In one embodiment, the soluble drug included in a drug coating according to the present invention is an opioid drug, with hydrocodone, oxycodone, hydromorphone, oxymorphone, and methadone being particularly preferred soluble drugs. Where the drug coating of the present invention includes a soluble drug, the soluble drug included in the drug coating preferably exhibits solubility that is at least as great as that of hydrocodone bitartrate at 25° C.

The film-forming agent included in a drug coating according to the present invention is water soluble and accounts for about 3 wt % to about 15 wt % of the drug coating, with drug coatings having about 7 wt % to about 10 wt % film-forming agent being preferred. The film-forming agent included in a drug coating according to the present invention is water soluble and preferably works to solubilize insoluble drug included in the drug coating. In addition, the film-forming agent included in a drug coating according to the present invention may be chosen such that the film-forming agent forms a solid solution with one or more insoluble drugs included in the drug coating. It is believed that drug loading and film forming characteristics of a drug coating according to the present invention are enhanced by selecting a film-forming agent that forms a solid solution with at least one of the one or more insoluble drugs included in the drug coating. A drug dissolved at the molecular level within the film-forming agent (a solid solution) is also expected to be more readily bioavailable because, as the drug coating breaks down or dissolves, the drug is released into the gastrointestinal tract and presented to the gastrointestinal mucosal tissue as discrete molecules.

In a preferred embodiment, the film-forming agent included in drug coating according to the present invention is a film-forming polymer or a polymer blend including at least one film-forming polymer. Polymer materials used as the film-forming agent of a drug coating of the present invention are water soluble. Examples of water soluble polymer materials that may be used as the film-forming polymer of a drug coating according to the present invention include, but are not limited to, hydroxypropylmethyl cellulose ("HPMC"), low molecular weight HPMC, hydroxypropyl cellulose ("HPC") (e.g., Klucel®), hydroxyethyl cellulose ("HEC") (e.g., Natrasol®), copovidone (e.g., Kollidon® VA 64), and PVA-PEG graft copolymer (e.g., Kollicoat® IR), and combinations thereof. A polymer blend or mixture may be used as the film forming agent of the present invention in order to achieve a drug coating having characteristics that may not be achievable using a single film-forming polymer in combination with the drug or drugs to be included in the drug coating. For example, blends of HPMC and copovidone provide a film-forming agent that allows the formation of drug coatings that not only exhibit desirable drug loading characteristics, but also provide coatings that are aesthetically pleasing and exhibit desirable physical properties.

A drug coating according to the present invention may also include a viscosity enhancer. Because the drug coating of the present invention is an aqueous coating that includes one or more insoluble drugs, the drug coating of the present invention is typically coated from an aqueous suspension formulation. In order to provide a drug coating with substantially uniform drug distribution from a suspension formulation, however, the suspension formulation should provide a substantially uniform dispersion of the insoluble drug included in the coating. Depending on the relative amounts and nature of the film-forming agent and the one or more drugs included in a drug coating according to the present invention, a viscosity enhancer may be included in a drug coating according to the present invention to facilitate the creation of a coating formulation that exhibits sufficient viscosity to provide a substantially uniform drug dispersion and facilitates the production of a drug coating according to the present invention having a substantially uniform distribution of insoluble drug. A viscosity enhancer included in a drug coating according to the present invention is preferably water-soluble and can be a film-forming agent. Examples of viscosity enhancers that may be used in a drug coating according to the present invention include, but are not limited to, HPC (e.g., Klucel®), HEC (e.g., Natrasol®), Polyox® water soluble resin products, and combinations thereof.

The precise amount of viscosity enhancing material included in a drug coating according to the present invention will vary, depending on the amounts and type of film-forming polymer and drug materials to be used in the drug coating. However, where included in a drug coating according to the present invention, a viscosity enhancer will typically account for 5 wt %, or less, of the drug coating. Preferably, a drug coating according to the present invention includes 2 wt %, or less, viscosity enhancer, and in particularly preferred embodiments, the drug coating according to the present invention includes 1 wt %, or less, viscosity enhancer.

The drug coating of the present invention may also include a disintegrating agent that increases the rate at which the drug coating disintegrates after administration. Because the drug coating of the present invention typically includes a large amount of insoluble drug, the drug coating may not break down or disintegrate as rapidly as desired after administration. A disintegrating agent included in a coating according to the present invention is a water swellable material that works to structurally compromise the coating as the disintegrating agent absorbs water and swells. Disintegrating agents that may be used in a drug coating according to the present invention include, but are not limited to modified starches, modified cellulose, and cross-linked polyvinylpyrrolidone materials. Specific examples of disintegrating agents that may be used in the drug coating of the present invention and are commercially available include Ac-Di-Sol®, Avicel®, and PVP XL-10. Where included in a drug coating according to the present invention, a disintegrating agent typically accounts for up to about 6 wt % of the coating, with coatings incorporating from about 0.5 wt % to about 3 wt % being preferred and coatings incorporating from about 1 wt % to about 3 wt % being particularly preferred.

The drug coating according to the present invention may also include a surfactant to increase the rate at which the drug coating dissolves or erodes after administration. The surfactant serves as a "wetting" agent that allows aqueous liquids to more easily spread across or penetrate the drug coating. Surfactants suitable for use in a drug coating according to the present invention are preferably solid at 25° C. Examples of surfactants that may be used in a drug coating of the present invention include, but are not limited to, surface active polymers, such as Poloxamer and Pluronic® surfactants. Where a surfactant is included in a drug coating according to the present invention, the surfactant will typically account for up to about 6 wt % of the drug coating, with drug coatings including about 0.5 wt % to about 3 wt % surfactant being preferred, and drug coatings including about 1 wt % to about 3 wt % surfactant being particularly preferred.

In one embodiment of the drug coating of the present invention, the film-forming agent includes a polymer blend formed of copovidone and HPMC. Where such a polymer blend is used as the film-forming agent of the drug coating of the present invention, the amounts of copovidone and HPMC may vary, as desired, to achieve a drug coating having desired physical and drug-loading characteristics. However, where the film-agent included in a drug coating according to the present invention is formed of a blend of copovidone and HPMC, the copovidone and HPMC are preferably included at a wt/wt ratio about 0.6:1 to about 0.7:1 copovidone to HPMC, with a wt/wt ratio of 1:1.5 being most preferred. Blends of HPMC and copovidone provide drug coatings that are aesthetically pleasing and are believed to be sufficiently robust to withstand further processing and an extended shelf life. Moreover, it is believed that copovidone can work to solubilize insoluble drug included in a drug coating according to the present invention, providing a drug coating that includes a solid solution of insoluble drug.

In another embodiment, the drug coating of the present invention includes a blend of HPMC and copovidone as the film-forming agent, and a non-steroidal anti-inflammatory drug (NSAID) as an insoluble drug. NSAIDs that may be included in a drug coating according to the present invention include, but are not limited to, ibuprofen, acetaminophen and naproxen. NSAIDs are widely used as analgesics, anti-inflammatories, and anti-pyretics, and such compounds can be combined with a variety of different soluble drugs to obtain multi-symptom relief from a variety of different ailments. For example, a drug coating according to the present embodiment may include an NSAID in combination with one or more soluble analgesics, antihistamines or antitussive, or antinausea agents.

In yet another embodiment, the drug coating of the present invention includes a blend of HPMC and copovidone as the film-forming agent, an insoluble NSAID, and a soluble narcotic drug, such as an opiate or opioid drug. In a specific example of such an embodiment, the drug coating includes an opioid drug, such as hydrocodone. A dosage form that includes the combination of acetaminophen or ibuprofen with an opiate or opioid drug provides a combination of analgesic, anti-inflammatory, anti-pyretic, and antitussive actions.

In even further embodiments, a drug coating according to the present invention includes a blend of HPMC and copovidone as the film-forming agent, an insoluble NSAID, a soluble narcotic drug, such as an opiate or opioid drug, and a viscosity enhancing agent or a disintegrating agent. In a specific example of such an embodiment, the drug coating includes between about 1 wt % and about 2 wt % of a viscosity enhancing agent, such as HPC. In another example of such an embodiment, the drug coating includes between about 0.5 wt % and about 3 wt % disintegrating agent, and in yet another example of such an embodiment, the drug coating includes between about 0.5 wt % and about 3 wt % of a surfactant.

A drug coating according to the present invention is not only capable of achieving high drug loading, but where the drug coating according to the present invention includes two or more different drugs, it has been found that a drug coating according to the present invention provides releases the different drugs in amounts that are directly proportional to the amounts of the drugs included in the drug coating. This is true even where drugs exhibiting drastically different solubility characteristics, such as acetaminophen and hydrocodone bitartrate (HBH), are included in the drug coating. In addition a drug coating according to the present invention releases substantially all of the drug included therein. Such performance characteristics facilitate reliable and predictable drug delivery performance, and allow formulation of drug coatings according to the present invention that deliver two or more drugs at a wide range of different ratios.

In another aspect, the present invention is directed to a coating formulation. A coating formulation according to the present invention can be used to provide a drug coating according to the present invention. The coating suspension of the present invention includes the materials used to form a drug coating of the present invention dissolved or suspended, depending on the material, within one or more solvents or solutions. The one or more solvents included in a coating suspension according to the present invention are not organic solvents, and are preferably aqueous solvents. Aqueous solvents that may be used in a coating suspension according to the present invention include, but are not limited to, purified water, pH adjusted water, acidified water, or aqueous buffer solutions. In a preferred embodiment, the aqueous solvent included in a coating suspension according to the present invention is purified water USP. The coating formulation of the present invention, therefore, is preferably an aqueous formulation and avoids the potential problems and disadvantages that can result from the use of organic solvents in formulating coating compositions.

As a drug coating according to the present invention includes at least one insoluble drug, the coating formulation of the present invention is typically prepared as an aqueous suspension using any suitable process, and in preferred embodiments the coating formulation of the present invention is formulated to facilitate production of drug coatings according to the present invention through a known coating process, such as, for example, known pan coating, fluid bed coating, or any other standard coating processes suitable for providing a drug coating. Though the precise amount of solvent used in a coating suspension according to the present invention may vary depending on, for example, the materials to be included in the finished drug coating, the desired coating performance of the coating suspension and the desired physical characteristics of the finished drug coating, a coating suspension according to the present invention typically includes up to about 30 wt % solids content, with the remainder of the coating suspension consisting of the desired solvent. A preferred embodiment of a coating suspension of the present invention includes about 80 wt % of a desired aqueous solvent and about 20 wt % solids content. The coating suspension of the present invention is formulated to exhibit a viscosity that is low enough to facilitate spray coating of drug coating according to the present invention, yet is high enough to maintain a substantially uniform dispersion of the insoluble drug included in the coating suspension during a coating process.

Because a coating formulation of the present invention is used to create a drug coating according to the present invention, the solids included in a coating suspension include materials useful in forming a drug coating according to the present invention. Therefore, the solids included in a coating suspension according to the present invention include at least one insoluble drug and a film-forming agent. The solids included in a coating suspension according to the present invention may also include a viscosity enhancer, a surfactant, or a disintegrating agent. As is true of a drug coating according to the present invention, a coating suspension according to the present invention may include two or more insoluble drugs or one or more insoluble drugs in combination with one or more soluble drugs.

In preparing a coating formulation according to the present invention, the drug loaded into the coating formulation may be provided in micronized form. By reducing the particle size of the drug loaded into a coating formulation according to the present invention, a more cosmetically smooth drug coating may be achieved. In addition, by reducing the particle size of the drug material loaded into a coating formulation according to the present invention, the dissolution rate of the drug when released from the drug coating prepared by the coating formulation may be improved, particularly where the drug is an insoluble drug. In one embodiment of the coating formulation of the present invention, the coating formulation includes a micronized drug material exhibiting an average particle size of less than 100 microns. In another embodiment, the coating formulation of the present invention includes a micronized drug material exhibiting an average particle size of less than 50 microns, and in yet another embodiment, the coating formulation of the present invention includes a micronized drug material exhibiting an average particle size of less than 10 microns. Micronization of the drug material can be readily achieved through processes well known in the art, such as, for example, known bead milling, jet milling or microprecipitation processes, and particle size can be measured using any conventional particle size measuring technique, such as sedimentation field flow fractionation, photon correlation spectroscopy or disk cetrifugation.

The solids dissolved or suspended in a coating formulation according to the present invention are loaded into the coating formulation in the same relative amounts as are used in a drug coating according to the present invention. For example, the drug included in a coating formulation of the present invention accounts for about 85 wt % to about 97 wt % of the solids loaded into the coating formulation. In preferred embodiments, the drug included in a coating formulation of the present invention accounts for about 90 wt % to about 93 wt % of the solids loaded into the coating formulation. The film-forming agent included in a coating formulation of the present invention accounts for about 3 wt % to about 15 wt % of the solids loaded into the coating formulation, and in preferred embodiments, the film-forming agent included in a coating formulation of the present invention accounts for about 7 wt % to about 10 wt % of the solids loaded into the coating formulation. Where included, a viscosity enhancer will typically account for 5 wt %, or less, of the solids included in a coating formulation of the present invention. Coating formulations wherein the viscosity enhancer accounts for 2 wt %, or less, of the solids are preferred, and in particularly preferred embodiments, a viscosity enhancer included in a coating formulation of the present invention accounts for 1 wt %, or less, of the solids included in the coating formulation. If the coating to be formed by the coating formulation is to include a disintegrating agent, the disintegrating agent typically accounts for up to about 6 wt % of the solids included in the coating formulation. In preferred embodiments, a disintegrating agent will account for about 0.5 wt % to about 3 wt % of the solids included in the coating formulation, and in particularly preferred embodiments of a coating formulation including a disintegrating agent, the disintegrating agent accounts for about 1 wt % to about 3 wt % of the solids included in the coating formulation. Where a surfactant is included in a drug coating according to the present invention, the surfactant will typically account for up to about 6 wt % of the solids included in the coating formulation. Preferably, if a surfactant is included in a coating formulation of the present invention, the surfactant will account for about 0.5 wt % to about 3 wt % of the solids included in the coating formulation, and in particularly preferred embodiments of a coating formulation according to the present invention that includes a surfactant, the surfactant accounts for about 1 wt % to about 3 wt % of the solids included in the coating formulation.

In yet another aspect, the present invention is directed to a dosage form. A dosage form according to the present invention includes a core coated by a drug coating according to the present invention. The core included in a dosage form according to the present invention can take on a variety of forms and may be formulated to include one or drugs to be delivered after dissolution or degradation of the drug coating. Where the core of a dosage form includes one or more drugs, such drugs may be the same as or different from the one or more drugs included in the drug coating. Such flexibility in the design and formulation of the dosage form of the present invention facilitates the creation of dosage forms capable of delivering a wide range of drugs or combinations of drugs to achieve a variety of different therapeutic results.

In one embodiment, the core included in a dosage form according to the present invention may be a pill, particle, pellet, bead, or spheroid, such as nu pareil beads (collectively referred to simply as "pills"). A pill used as a core in a dosage form of the present invention may be formed of a variety of different materials. Moreover, where the dosage form of the present invention includes a core formed by a pill, the pill may be formulated to be free of active agent or to include one or more active agents, as desired. Materials useful for forming a pill to be used as a core in a dosage form of the present invention include, but are not limited to, polymer materials, such as plastic resins, inorganic substances, such as silica, glass, hydroxyapatite, salts (e.g., sodium or potassium chloride, calcium or magnesium carbonate) and the like, organic substances, such as activated carbon, acids (e.g., citric acid, fumaric acid, tartaric acid, or ascorbic acid) and the like, and saccharides and derivatives thereof. Particularly suitable materials for forming a pill for use as a core in a dosage form of the present invention include saccharides such as sugars, oligosaccharides, polysaccharides and their derivatives, such as glucose, rhamnose, galactose, lactose, sucrose, mannitol, sorbitol, destrin, maltodextrin, cellulose, microcrystalline cellulose, sodium carboxymethyl cellulose, starches (e.g., corn starch, rice starch, potato starch, wheat starch, or tapioca starch) and the like. Generally, the core forming materials discussed herein may be used to form pills that are either free from of drug or include one or more soluble or insoluble drugs, as desired.

In another embodiment, the dosage form of the present invention includes a core formed using a tablet or capsule. The tablet or capsule included in such an embodiment can take on virtually any desired size or shape and may be manufactured using a wide range of known materials. However, where the core of the dosage form of the present invention includes a tablet or capsule, the table or capsule is preferably manufactured of materials that are suitable for oral delivery to a desired animal or human subject and tablet or capsule is preferably sized and shaped to facilitate oral delivery. For example, where the core includes a soft capsule or "soft-cap" and the dosage form is intended for oral delivery to a human subject, the soft-cap preferably exhibits a size ranging from about 3 to about 22 minims, with 1 minim being equal to 0.0616 ml, and the soft-cap may be provided, for example, in standard oval or oblong shapes. In yet another example, where the core of a dosage form of the present invention includes a hard capsule or "hard-cap" and is intended for oral delivery to human subject, the hard-cap is preferably provided in one of the various standard sizes designated as (000), (00), (0), (1), (2), (3), (4), and (5). Although capsules and tablets exhibiting standard shapes and sizes are presently preferred due to their ready commercial availability, the core of a dosage form of the present can be formed using tablets or capsules of non-standard size or shape suited to a desired delivery application.

Further, where a dosage form according to the present invention includes a core formed using a tablet or capsule, the tablet or capsule included in the core is preferably formulated or configured to provide a controlled release dosage form. The subsequent coating of such a core with a drug coating according to the present invention formulated to provide the immediate release of one or more drugs provides a dosage form exhibiting the performance advantages of both an immediate release dosage form and a controlled release dosage form. Controlled release dosage forms that may be used to form the core of a dosage form of the present invention include, but are not limited to, dosage forms well known in the art, such as controlled release dosage forms that include a tableted matrix, controlled release matrix dosage forms that include a tableted matrix and are banded with one or more insoluble bands to provided controlled release, and osmotically driven dosage forms. Examples of controlled release dosage forms that may serve as a core of a dosage form of the present invention include, but are not limited to, the dosage forms described in U.S. Pat. Nos. 4,235,236, 4,278,087, 4,663,149, 4,777,049, 4,801,461, 4,854,470, 4,961,932, 5,023,088, 5,030,456, 5,221,536, 5,245,357, 5,512,299, 5,534,263, 5,614,578, 5,667,804, 5,830,502, 5,858,407, 5,906,832, 5,948,747, 6,020,000, 6,153,678, 6,174,547, 6,183,466, 6,245,357, 6,316,028, and 6,365,183; U.S. Patent Publications numbered US2003-0198619, US2003-0232078, and US2002-0071863; PCT Publications numbered WO 95/34285 and WO 04/02448; and PCT Application numbered US04/24921 (not yet published), the contents of each of which are incorporated herein in their entirety by reference.

The drug coating included in a dosage form of the present invention can be formed over the core included in the dosage form using coating processes known in the art. Moreover, a drug coating included in a dosage form of the invention can be formed using a coating formulation as described herein. Suitable processes for creating a drug coating in a dosage form of the present invention include any standard coating process suitable for providing a drug coating and include, but are not limited to, known pan coating and fluid bed coating processes.

Though the dosage form of the present invention includes a core coated by a drug coating according the present invention, the drug coating is not necessarily the outermost coating of the dosage form. For example, where desired, the drug coating included in a dosage form according to the present invention may be coated with a color coat or another finish coat to provide a final dosage form. Alternatively, a drug coating included in a dosage form of the present invention could be coated with another drug coating, or even a coating designed to cause dissolution or degradation of the drug coating at a specified location within the gastrointestinal tract of an intended subject, such as an enteric coating, or at a desired time post-administration. Moreover, even though the drug coating included in a dosage form according to the present invention is provided over a core, the drug coating need not be immediately adjacent the core. Regardless of whether the core is formed using a pill, a tablet, or a capsule, one or more material layers may intervene between the drug coating and the core-forming material or structure. Such intervening layers may be included to facilitate better function of either the core forming material or the drug coating. Alternatively, intervening material layers may ease production of the drug coating or, where desirable, prevent interaction between the core and the drug composition.

EXAMPLE 1

A drug coating according to the present invention was provided over placebo dosage forms. The coating included 7.2 wt % film-forming agent formed of a blend of HPMC E5 (supplied by Dow) and copovidone (Kollidon® VA 64, supplied by BASF). The HPMC accounted for 4.3 wt % of the drug coating, and the Kollidon® VA 64 accounted for 2.9 wt % of the drug coating. Ibuprofen USP was the drug included in the drug coating, and the ibuprofen USP accounted for 92.8 wt % of the drug coating.

In order to form the drug coating, an aqueous coating formulation was created using purified water USP as the solvent. The coating formulation included a solids content of 24 wt % and a solvent content of 76 wt %. The solids loaded into the coating formulation were those that formed the finished drug coating, and the solids were loaded in the coating formulation in the same relative proportions as contained in the finished drug coating. The coating formulation was mixed using standard procedures to achieve a substantially uniform coating formulation. The coating formulation was prepared as a 2,977.5 gram batch.

After forming the coating formulation, the drug coating was formed over the placebo dosage forms using a Vector LDCS pan coater. The pump included in the coater was a Masterflex® peristaltic pump and the tubing used in the coater was Masterflex® 96410-16 tubing. The pan of the coater was charged with 1,800 g of the coating formulation, and the drug coating was coated over the placebo dosage forms under the conditions listed in Table 1. The placebo dosage forms were processed in the coater for 4.5 hours, resulting in the placebo dosage forms being coated with a drug coating weighing about 165 mg, on average.

TABLE 1

| Coating Conditions | |
| --- | --- |
| Pan Speed: | 21 RPM |
| Atom. Air Pressure: | 19 psi |
| Gun-to-Bed Dist: | 3.5" |
| Flow Rate: | 12 g/min |
| Nozzle: | 60100SS |
| Air Cap: | 120SS |
| Exhaust Temp: | 35° C.-45° C. |
| Pan Air Flow: | 35-36 CFM |

EXAMPLE 2

A drug coating according to the present invention was provided over placebo dosage forms. The coating included 17.8 wt % film-forming agent formed of a blend of HPMC E5 (supplied by Dow) and copovidone (Kollidon®VA 64, supplied by BASF). The HPMC accounted for 10.7 wt % of the drug coating and the Kollidon® VA 64 accounted for 7.1 wt % of the drug coating. The drug included in the coating was ibuprofen USP, and the ibuprofen USP accounted for 82.2 wt % of the drug coating.

In order to form the drug coating, an aqueous coating formulation was created using purified water USP as the solvent. The coating formulation included a solids content of 20 wt % and a solvent content of 80 wt %. The solids loaded into the coating formulation were those that formed the finished drug coating, and the solids were loaded in the coating formulation in the same relative proportions as contained in the finished drug coating. The coating formulation was mixed using standard procedures to achieve a substantially uniform coating formulation. The coating formulation was prepared as a 3978.4 gram batch.

After forming the coating formulation, the drug coating was provided over the placebo dosage forms using a Vector LDCS pan coater. The pump included in the coater was a Masterflex® peristaltic pump and the tubing used in the coater was Masterflex® 96410-16 tubing. The pan of the coater was charged with 1,800 g of the coating formulation, and the drug coating was coated over the placebo dosage forms under the conditions listed in Table 1. The placebo dosage forms were processed in the coater for 4.8 hours, resulting in the placebo dosage forms being coated with a drug coating weighing about 188 mg, on average.

EXAMPLE 3

A drug coating according to the present invention was provided over placebo dosage forms. The coating included 6.0 wt % film-forming agent formed of a blend of HPMC E5 (supplied by Dow) and copovidone (Kollidon® VA 64, supplied by BASF). The HPMC accounted for 3.6 wt % of the drug coating and the Kollidon® VA 64 accounts for 2.4 wt % of the drug coating. The drug coating also included HPC (Klucel® MF) as a viscosity enhancer. The HPC accounted for 1.5 wt % of the drug coating. The drug included in the drug coating was acetaminophen USP (APAP USP, supplied by BASF as a fine powder), and the APAP USP accounted for 92.5 wt % of the drug coating.

In order to form the drug coating, an aqueous coating formulation was prepared using purified water USP as the solvent. The coating formulation included a solids content of 20 wt % and a solvent content of 80 wt %. The solids loaded into the coating formulation were those that formed the finished drug coating, and the solids were loaded in the coating formulation in the same relative proportions as included in the finished drug coating. The coating formulation was mixed using standard procedures to achieve a substantially uniform coating formulation.

The drug coating was formed over the placebo dosage forms using a Vector LDCS pan coater. The pump included in the coater was a Masterflex® peristaltic pump, and the tubing used in the coater was Masterflex® 96410-16 tubing. The pan of the coater was charged with 1,800 g of the coating formulation, and the drug coating was coated over the dosage forms under the conditions listed in Table 1. The placebo dosage forms were processed in the coater for 3.75 hours, resulting in the placebo dosage forms being coated with a drug coating weighing about 183 mg, on average.

EXAMPLE 4

A drug coating according to the present invention was provided over placebo dosage forms. The coating included 6.6 wt % film-forming agent formed of a blend of HPMC E5 (supplied by Dow) and copovidone (Kollidon® VA 64, supplied by BASF). The HPMC accounted for 3.95 wt % of the drug coating and the Kollidon® VA 64 accounted for 2.65 wt % of the drug coating. The drug coating also included HPC (Klucel® MF) as a viscosity enhancer. The HPC accounted for 1.0 wt % of the drug coating. An insoluble drug and a soluble drug were included in the drug coating, with the two drugs accounting for 92.4 wt % of the drug coating. The insoluble drug included in the coating was APAP USP (supplied by BASF as a fine powder), which accounted for 90 wt % of the drug coating, and the soluble drug included in the coating was hydrocodone bitartrate (HBH), which accounted for 2.4 wt % of the drug coating.

In order to form the drug coating, an aqueous coating formulation was created using purified water USP as the solvent. The coating formulation included a solids content of 20 wt % and a solvent content of 80 wt %. The solids loaded into the coating formulation were those that formed the finished drug coating, and the solids were loaded in the coating formulation in the same relative proportions as contained in the finished drug coating. The coating formulation was mixed using the procedure outlined in Table 3 to obtain a substantially uniform coating formulation. The coating formulation was prepared as a 4,000 gram batch.

After forming the coating formulation, the drug coating was provided over the placebo dosage forms using a Vector LDCS pan coater. The pump included in the coater was a Masterflex® peristaltic pump and the tubing used in the coater was Masterflex® 96410-16 tubing. The pan of the coater was charged with 1,800 g of the coating formulation, and the drug coating was coated over the placebo dosage forms under the conditions listed in Table 1 until a coating of about 200 mg (average coating weight of 199.7 mg) was achieved.

TABLE 3

Coating Formulation Preparation

Vessel I

Tare the Vessel and turn mixer on.
Charge 1/3 water into the vessel.
While mixing, slowly charge the HPC into the vessel.
Continue mixing until the material is totally dissolved.

Vessel II

Tare the vessel, charge ¾ of water required into the vessel.
While mixing, slowly charge the Copovidone into the vessel.
Continue mixing until the material is dissolved.
While mixing, slowly charge the HPMC into the vessel.
Continue mixing until the material is dissolved.
Transfer the Vessel I solution into the Vessel II.
Mix until a clear solution results.
If including a disintegrant or a surfactant, add disintegrant or surfactant while mixing.
Mix until the solution is homogeneous.
While mixing, slowly charge the insoluble drug (e.g., APAP or ibuprofen) into the mixing vessel.
Continue mixing until no lumps are present.
Mix for at least two hours before use.
Determine the net amount of drug coating formulation prepared.
Continue mixing until the required amount of drug coating formulation is applied.
Do not allow a vortex to form.

EXAMPLE 5

Figure 2:
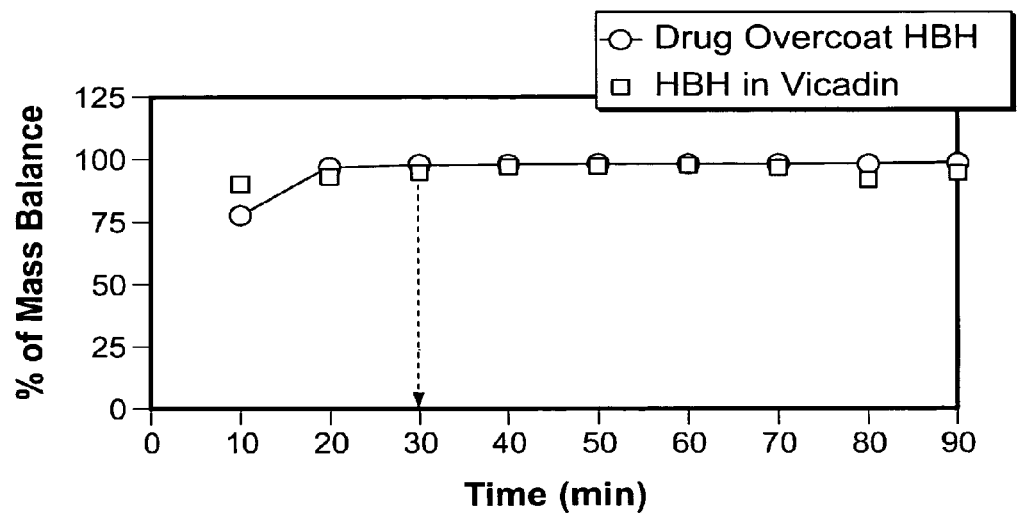
FIG. 2 provides a graph illustrating the dissolution rate of hydrocodone bitartrate (HBH) from a drug coating according to the present invention compared to the dissolution rate of HBH from a commercially available Vicodin® tablet.

The dissolution rates of both APAP and HBH from the drug coating prepared according to Example 4 was evaluated and compared with the dissolution rates provided by Vicodin® tablets. USP Type II equipment was used to evaluate the dissolution rates from the exemplary drug coating and from the Vicodin® tablets. As can be seen by reference to FIG. 1 and FIG. 2, the dissolution rates of both APAP and HBH from the exemplary drug overcoat were comparable to those provided by the Vicodin® tablets, with the $t_{90}$ of the APAP and HBH from the exemplary drug coating and from the Vicodin® tablets occurring within 30 minutes.

EXAMPLE 6

Figure 3:
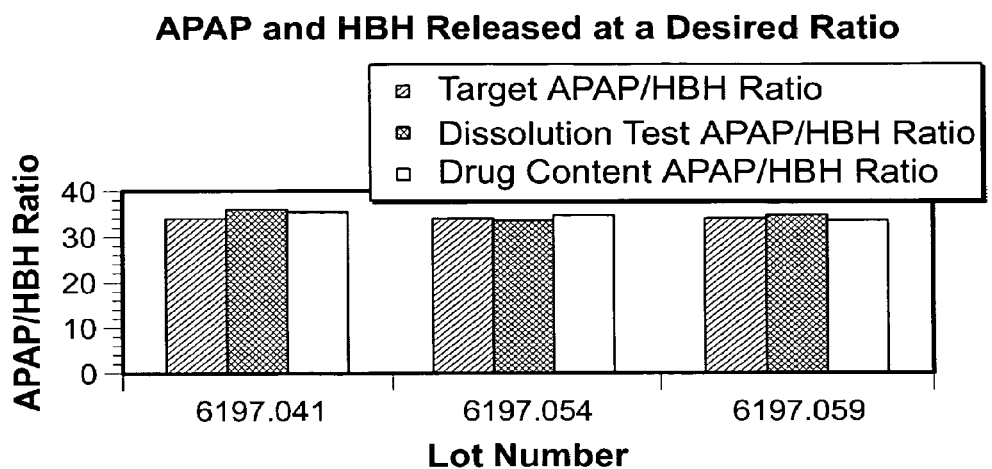
FIG. 3 provides a graph illustrating the ratio of APAP to HBH released from drug coatings according to the present invention, where the release ratio is determined by evaluating the dissolution profiles of APAP and HBH based on mass balance.

The dissolution profiles of APAP and HBH from drug coatings according to the present invention were evaluated based on mass balance. The target release ratio of APAP:HBH from the drug coating was 34:1. Three different lots of dosage forms having coatings according to present invention were evaluated. The results of such evaluation are provided in FIG. 3, and as can be seen from FIG. 3, the drug coatings according to the present invention provided desirable APAP and HBH release performance, with the drug coatings in each lot releasing the APAP and HBH at or very near the targeted release ratio.

ings were coated over the placebo dosage forms under the conditions listed in Table 1 until coatings provided the average weight gains detailed in Table 2.

In order to evaluate the dissolution rate of APAP from each of the four different coatings and from the NORCO® tablet, a USP Type II apparatus was used. The media used was 900 ml of acidified water maintained at 37° C., and the stir rate was 50 rpm. The amount of APAP present in the media was measured at 5-minute intervals over a period of 90 minutes using a standard UV assay technique.

Figure 4:
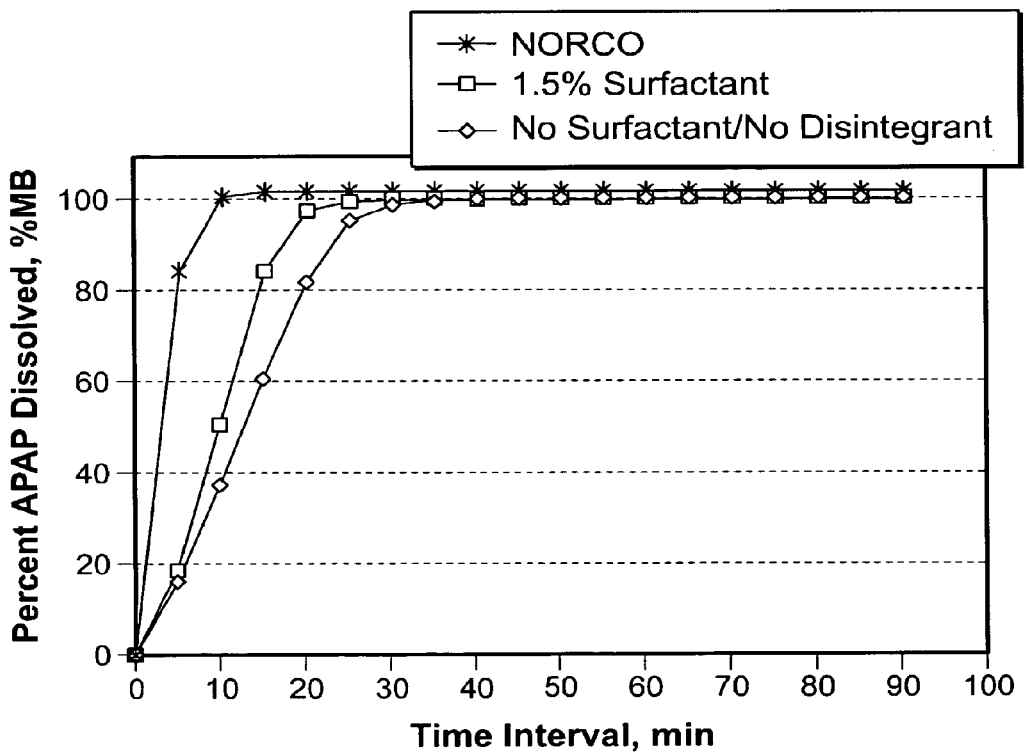
FIG. 4 provides a graph illustrating the dissolution rate of APAP from two different drug coatings according to the present invention compared to the dissolution rate of APAP from a commercially available NORCO® tablet.
Figure 5:
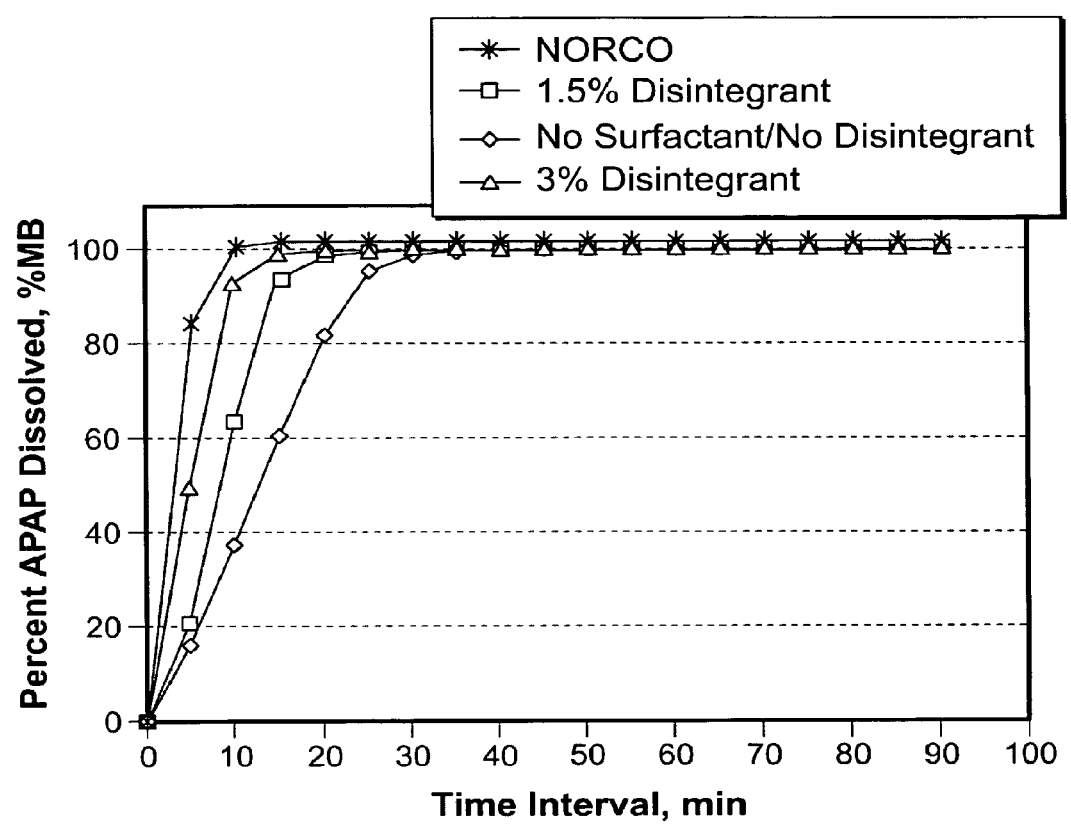
FIG. 5 provides a graph illustrating the dissolution rate of APAP from three different drug coatings according to the present invention compared to the dissolution rate of APAP from a commercially available NORCO® tablet.

The results of the dissolution testing are shown in FIG. 4 and FIG. 5. As can be seen by reference to FIG. 4 and FIG. 5, the inclusion of a surfactant or a disintegrating agent in a drug coating according to the present invention can provide measurable improvements in the rate at which drug is released from the drug coating. In the case of the disintegrating agent Ac-Di-Sol®, increasing the amount of Ac-Di-Sol® in the drug coating can provide an increase in the rate at which drug is dissolved from the coating, with the drug coating that includes 3.0 wt % Ac-Di-Sol® providing a dissolution rate approaching that provided by the NORCO® tablet.

TABLE 2

Drug Overcoat Formulations (Example 7)

| | | Formulation (wt %) | | | |
|---|---|---|---|---|---|
| Materials | Code | No Sufactant/ No Disintegrant | 1.5% Disentegrant | Surfactant | 3.0% Disentegrant |
| APAP | 0012590 | 90.00 | 90.00 | 90.00 | 88.00 |
| HBC (For Calculation Purposes Only) | 0011334 | 2.40 | 2.40 | 2.40 | 2.40 |
| Copovidone | 0011445 | 2.65 | 2.04 | 2.04 | 2.24 |
| HPMC 2910 | 0001634 | 3.95 | 3.06 | 3.06 | 3.36 |
| HPC | 0000614 | 1.00 | 1.00 | 1.00 | 1.00 |
| Ac-Di-Sol | 80142 | — | 1.50 | — | 3.00 |
| Poloxamer 188 | 4304 | — | — | 1.50 | — |
| Weight Gain | | 199.7 | 196.7 | 194.4 | 196.6 |
| Total APAP Dose | | 180 | 177 | 175 | 173 |

EXAMPLE 7

The dissolution rates of APAP from four different drug coatings according to the present invention were compared to the dissolution rate of APAP from a commercially available NORCO® tablet. The formulations of each of the four different drug coatings are provided in Table 2. HBH was included in Table 2 for calculation purposes only. The HBH was not included in any of the four coating formulations prepared in this Example.

In order to form each of the four different drug coatings, four different aqueous coating formulations were prepared using purified water USP as the solvent. Each of the four coating formulations included a solids content of 20 wt % and a solvent content of 80 wt %. Each of the four coating formulations was loaded with the solids used to form one of the four different coating formulations. The coating formulations were mixed using procedure outlined in Table 3 to achieve substantially uniform coating formulations.

After forming the coating formulations, the four drug coatings were provided over the placebo dosage forms using a Vector LDCS pan coater. The pump included in the coater was a Masterflex® peristaltic pump and the tubing used in the coater was Masterflex® 96410-16 tubing. During each coating process, the pan of the coater was charged with 1,800 g of the desired coating formulation. The four different drug coat-

EXAMPLE 8

A drug coating according to the present invention including a surfactant was formed over placebo dosage forms. The coating included 5.1 wt % film-forming agent formed of a blend of HPMC 2910 and copovidone (Kollidon® VA 64, supplied by BASF). The HPMC accounted for 3.06 wt % of the drug coating and the Kollidon® VA 64 accounted for 2.04 wt % of the drug coating. The drug coating also included HPC (Klucel® MF) as a viscosity enhancer, and Poloxamer 188 as a surfactant. The HPC accounted for 1.0 wt % of the drug coating, and the Poloxamer accounted for 1.5 wt % of the drug coating. An insoluble drug and a soluble drug were included in the drug coating, with the two drugs accounting for 92.4 wt % of the drug coating. The insoluble drug included in the coating was APAP USP (supplied by BASF as a fine powder), which accounted for 90 wt % of the drug coating, and the soluble drug included in the coating was HBH, which accounted for 2.4 wt % of the drug coating.

In order to form the drug coating, an aqueous coating formulation was created using purified water USP as the solvent. The coating formulation included a solids content of 20 wt % and a solvent content of 80 wt %. The solids loaded into the coating formulation were those that formed the finished drug coating, and the solids were loaded in the coating formulation in the same relative proportions as contained in the finished drug coating. The coating formulation was mixed using the procedure outlined in Table 3 to achieve a substantially uniform coating formulation.

After forming the coating formulation, the drug coating was provided over the placebo dosage forms using a Vector LDCS pan coater. The pump included in the coater was a Masterflex® peristaltic pump and the tubing used in the coater was Masterflex® 96410-16 tubing. The pan of the coater was charged with 1,800 g of the coating formulation, and the drug coating was coated over the placebo dosage forms under the conditions listed in Table 1 until a drug coating of about 200 mg (average coating weight of 194.4 mg) was achieved.

EXAMPLE 9

A drug coating according to the present invention including a disintegrating agent was formed over placebo dosage forms. The coating included 5.1 wt % film-forming agent formed of a blend of HPMC 2910 and copovidone (Kollidon® VA 64, supplied by BASF). The HPMC accounted for 3.06 wt % of the drug coating and the Kollidon® VA 64 accounted for 2.04 wt % of the drug coating. The drug coating also included HPC (Klucel® MF) as a viscosity enhancer, and Ac-Di-Sol® as a disintegrating agent. The HPC accounted for 1.0 wt % of the drug coating, and the Ac-Di-Sol® accounted for 1.5 wt % of the drug coating. An insoluble drug and a soluble drug were included in the drug coating, with the two drugs accounting for 92.4 wt % of the drug coating. The insoluble drug included in the coating was APAP USP (supplied by BASF as a fine powder), which accounted for 90 wt % of the drug coating, and the soluble drug included in the coating was HBH, which accounted for 2.4 wt % of the drug coating.

In order to form the drug coating, an aqueous coating formulation was created using purified water USP as the solvent. The coating formulation included a solids content of 20 wt % and a solvent content of 80 wt %. The solids loaded into the coating formulation were those that formed the finished drug coating, and the solids were loaded in the coating formulation in the same relative proportions as contained in the finished drug coating. The coating formulation was mixed using the procedure outlined in Table 3 to achieve a substantially uniform coating formulation.

After forming the coating formulation, the drug coating was provided over the placebo dosage forms using a Vector LDCS pan coater. The pump included in the coater was a Masterflex® peristaltic pump and the tubing used in the coater was Masterflex® 96410-16 tubing. The pan of the coater was charged with 1,800 g of the coating formulation, and the drug coating was coated over the placebo dosage forms under the conditions listed in Table 1 until a drug coating of about 200 mg (average coating weight of 196.7 mg) was achieved.

EXAMPLE 10

A drug coating according to the present invention including a disintegrating agent is prepared and coated onto a dosage form. The coating includes 5.6 wt % film-forming agent formed of a blend of HPMC 2910 and copovidone (Kollidon® VA 64, supplied by BASF). The HPMC accounts for 3.36 wt % of the drug coating and the Kollidon® VA 64 accounts for 2.24 wt % of the drug coating. The drug coating also includes HPC (Klucel® MF) as a viscosity enhancer, and Ac-Di-Sol® as a disintegrating agent. The HPC accounts for 1.0 wt % of the drug coating, and the Ac-Di-Sol® accounts for 3.0 wt % of the drug coating. An insoluble drug and a soluble drug are included in the drug coating, with the two drugs accounting for 90.4 wt % of the drug coating. The insoluble drug included in the coating is APAP USP (supplied by BASF as a fine powder), which accounts for 88.0 wt % of the drug coating, and the soluble drug included in the coating is HBH, which accounts for 2.4 wt % of the drug coating.

An aqueous coating formulation is created using purified water USP as the solvent. The coating formulation includes a solids content of 20 wt % and a solvent content of 80 wt %. The solids loaded into the coating formulation are those that form the finished drug coating, and the solids are loaded in the coating formulation in the same relative proportions will be exhibited in the finished drug coating. The coating formulation is mixed using the procedure outlined in Table 3 to achieve a substantially uniform coating formulation.

After forming the coating formulation, the drug coating is provided over the dosage forms using a Vector LDCS pan coater. The pump included in the coater is any suitable pump, such as a Masterflex® peristaltic pump, and the tubing used in the coater is any suitable tubing, such as Masterflex® 96410-16 tubing. The pan of the coater is charged with a desired amount of the coating formulation, and the drug coating is coated over the dosage forms under the conditions listed in Table 1 until a drug coating of a desired weight is achieved.

EXAMPLE 11

A drug coating according to the present invention is provided over a dosage form. The coating includes 7.0 wt % film-forming agent formed of a blend of HPMC E5 (supplied by Dow) and copovidone (Kollidon® VA 64, supplied by BASF). The HPMC accounts for 4.2 wt % of the drug coating, and the Kollidon® VA 64 accounts for 2.8 wt % of the drug coating. The drug coating includes an insoluble drug and a soluble drug, with the total drug content of 93 wt %. The insoluble drug included in the coating is ibuprofen USP, which accounts for 90 wt % of the drug coating, and the soluble drug included in the coating is HBH, which accounts for 3 wt % of the drug coating.

To form the drug coating, an aqueous coating formulation is prepared using purified water USP as the solvent. The coating formulation includes a solids content of 25 wt % and a solvent content of 75 wt %. The solids loaded into the coating formulation are those that form the finished drug coating, and the solids are loaded in the coating formulation in the same relative proportions as will be exhibited in the finished drug coating. The coating formulation is mixed using standard procedures to achieve a substantially uniform coating formulation.

The drug coating is formed over the dosage forms using any suitable coater, such as a Vector LDCS pan coater. The pump included in the coater is any suitable pump, such as a Masterflex® peristaltic pump, and the tubing used in the coater is any suitable tubing, such as Masterflex® 96410-16 tubing. The pan of the coater is charged with a desired amount of the coating formulation, and the drug coating is coated over the placebo dosage forms under the conditions listed in Table 1 until a drug coating of a desired weight is achieved.

EXAMPLE 12

A drug coating according to the present invention is formed over a dosage form. The coating includes 17.3 wt % film-forming agent formed of a blend of HPMC E5 (supplied by Dow) and copovidone (Kollidon® VA 64, supplied by BASF). The HPMC accounts for 10.4 wt % of the drug coating and the Kollidon® VA 64 accounts for 6.9 wt % of the drug coating. The drug coating includes an insoluble drug and a soluble drug, with the total drug content of 82.7 wt %. The insoluble drug included in the coating is ibuprofen USP, which accounts for 80 wt % of the drug coating, and the soluble drug included in the coating is HBH, which accounts for 2.7 wt % of the drug coating.

To form the drug coating, an aqueous coating formulation is prepared using purified water USP as the solvent. The coating formulation includes a solids content of 20 wt % and a solvent content of 80 wt %. The solids loaded into the coating formulation are those that form the finished drug coating, and the solids are loaded in the coating formulation in the same relative proportions as will be exhibited in the finished drug coating. The coating formulation is mixed using standard procedures to achieve a substantially uniform coating formulation.

The drug coating is provided over the dosage forms using any suitable coater, such as a Vector LDCS pan coater. The pump included in the coater is any suitable pump, such as a Masterflex® peristaltic pump, and the tubing used in the coater is any suitable tubing, such as Masterflex® 96410-16 tubing. The pan of the coater is charged with a desired amount of the coating formulation, and the drug coating is coated over the dosage forms under the conditions listed in Table 1 until a drug coating of a desired weight is achieved.

EXAMPLE 13

A drug coating according to the present invention is provided over a dosage form. The coating includes 5.85 wt % film-forming agent formed of a blend of HPMC E5 (supplied by Dow) and copovidone (Kollidon® VA 64, supplied by BASF). The HPMC accounts for 3.5 wt % of the drug coating and the Kollidon® VA 64 accounts for 2.35 wt % of the drug coating. The drug coating also includes HPC (Klucel® MF) as a viscosity enhancer. The HPC accounts for 1.5 wt % of the drug coating. An insoluble drug and a soluble drug are included in the drug coating, with the two drugs accounting for 92.65 wt % of the drug coating. The insoluble drug included in the coating is acetaminophen, which accounts for 90 wt % of the drug coating, and the soluble drug included in the coating is HBH, which accounts for 2.65 wt % of the drug coating.

In order to form the drug coating, an aqueous coating formulation is prepared using purified water USP as the solvent. The coating formulation includes a solids content of 20 wt % and a solvent content of 80 wt %. The solids loaded into the coating formulation are those that form the finished drug coating, and the solids are loaded in the coating formulation in the same relative proportions as will be exhibited in the finished drug coating. The coating formulation is mixed using the procedure outlined in Table 3 to achieve a substantially uniform coating formulation.

The drug coating is formed over the dosage forms using any suitable coater, such as a Vector LDCS pan coater. The pump included in the coater is any suitably pump, such as a Masterflex® peristaltic pump, and the tubing used in the coater may be any suitable tubing, such as Masterflex® 96410-16 tubing. The pan of the coater is charged with a desired amount of the coating formulation, and the drug coating is coated over the dosage forms under the conditions listed in Table 1 until a coating of desired weight is achieved.

What is claimed is:

1. A dosage form comprising:
    an osmotic core comprising hydrocodone; and
    a coating comprising
        acetaminophen,
        hydrocodone,
        hydroxypropyl cellulose, and
        a water soluble film former comprising hydroxypropyl methylcellulose, copovidone, a film-forming agent that forms a solid solution with the acetaminophen, or blends thereof;
    wherein the acetaminophen is present in the coating in an amount ranging from about 60 wt % to about 97 wt % based on the total weight of the coating, and the water soluble film former accounts for about 3 wt % to about 15 wt % based on the total weight of the coating.

2. The dosage form of claim 1, wherein the coating further comprises a viscosity enhancer, surfactant, or a disintegrating agent.

3. The dosage form of claim 1, wherein the water soluble film former comprises a blend of hydroxypropyl methylcellulose and copovidone.

4. The dosage form of claim 3, wherein the wt/wt ratio of copovidone to hydroxypropyl methylcellulose is about 1:1.5.

* * * * *